(12) United States Patent
Julien et al.

(10) Patent No.: US 11,986,665 B2
(45) Date of Patent: May 21, 2024

(54) IMPLANTABLE LEAD

(71) Applicant: SORIN CRM S.A.S., Clamart (FR)

(72) Inventors: Etienne Julien, Paris (FR); Nicolas Shan, Antony (FR); Maxime Rault, Paris (FR)

(73) Assignee: SORIN CRM SAS, Clamart (FR)

( * ) Notice: Subject to any disclaimer, the term of this patent is extended or adjusted under 35 U.S.C. 154(b) by 0 days.

(21) Appl. No.: 16/688,844

(22) Filed: Nov. 19, 2019

(65) Prior Publication Data
US 2020/0155855 A1 May 21, 2020

(30) Foreign Application Priority Data
Nov. 21, 2018 (FR) ...................................... 1871664

(51) Int. Cl.
*A61N 1/375* (2006.01)
*A61N 1/05* (2006.01)
*A61N 1/36* (2006.01)
*A61N 1/39* (2006.01)

(52) U.S. Cl.
CPC ......... *A61N 1/3752* (2013.01); *A61N 1/0565* (2013.01); *A61N 1/3605* (2013.01); *A61N 1/37512* (2017.08); *A61N 1/39* (2013.01)

(58) Field of Classification Search
None
See application file for complete search history.

(56) References Cited

U.S. PATENT DOCUMENTS

| 3,769,984 | A | * | 11/1973 | Muench | A61N 1/056 607/122 |
| 5,626,491 | A | | 5/1997 | Hasircoglu | |
| 5,984,711 | A | * | 11/1999 | Woodard | H01R 13/5224 29/257 |
| 6,293,594 | B1 | * | 9/2001 | Safarevich | A61N 1/05 174/84 R |
| 6,697,675 | B1 | * | 2/2004 | Safarevich | A61N 1/05 607/116 |
| 7,520,763 | B1 | | 4/2009 | Buse | |

(Continued)

FOREIGN PATENT DOCUMENTS

| CN | 106232181 A | 12/2016 |
| CN | 108348747 A | 7/2018 |

(Continued)

OTHER PUBLICATIONS

First office action on Chinese Application No. 201911147244.1 dated Nov. 2, 2020. 14 pages.

(Continued)

*Primary Examiner* — Erica S Lee

(57) ABSTRACT

The present invention relates to an implantable lead comprising at least one conductive wire and one electrical connector, the electrical connector configured to be connected to an implantable medical device such as a cardiac stimulation, defibrillation and/or neuromodulation device, wherein the electrical connection between the conductive wire and the connector is effected by a first hypotube welded to the conductive wire and welded to a second hypotube of the electrical connector. The present invention also relates to a method for electrically connecting the at least one conductive wire of the implantable lead to the electrical connector.

11 Claims, 3 Drawing Sheets

(56) References Cited

U.S. PATENT DOCUMENTS

| | | |
|---|---|---|
| 7,680,544 B1 | 3/2010 | Conger |
| 8,295,948 B2 | 10/2012 | Barker et al. |
| 8,417,343 B2 | 4/2013 | Bolea et al. |
| 8,939,905 B2 | 1/2015 | Schugt et al. |
| 8,968,331 B1 * | 3/2015 | Sochor ............... A61B 17/3468 606/129 |
| 2004/0064174 A1 * | 4/2004 | Belden ................. H01R 13/187 607/122 |
| 2005/0222634 A1 | 10/2005 | Flickinger et al. |
| 2009/0018393 A1 * | 1/2009 | Dick .................... A61B 5/0066 600/109 |
| 2010/0121421 A1 | 5/2010 | Duncan et al. |
| 2010/0179627 A1 | 7/2010 | Floyd et al. |
| 2011/0009934 A1 | 1/2011 | Conger |
| 2011/0022142 A1 | 1/2011 | Barker et al. |
| 2011/0220408 A1 * | 9/2011 | Walsh ...................... A61N 1/05 174/75 R |
| 2011/0257659 A1 | 10/2011 | Mehdizadeh et al. |
| 2012/0167385 A1 * | 7/2012 | McGiboney ......... A61N 1/3752 29/846 |
| 2013/0005169 A1 | 1/2013 | Soltis et al. |
| 2014/0058276 A1 | 2/2014 | Bodecker et al. |
| 2015/0165217 A1 | 6/2015 | Hughes |
| 2016/0158558 A1 | 6/2016 | Shanahan et al. |
| 2016/0287862 A1 * | 10/2016 | Shan .................. A61N 1/36125 |
| 2016/0296749 A1 * | 10/2016 | Farr ....................... H01R 43/16 |
| 2018/0165217 A1 | 6/2018 | Greenspan |

FOREIGN PATENT DOCUMENTS

| | | |
|---|---|---|
| EP | 1 426 079 | 6/2004 |
| EP | 2 571 569 | 3/2013 |
| EP | 3 075 411 A1 | 10/2016 |
| WO | WO-2011/145084 | 11/2011 |
| WO | WO-2017/191507 | 11/2017 |

OTHER PUBLICATIONS

French Search Report for French Application No. 1871664 dated Sep. 11, 2019, 1 page.

French Search Report for French Application No. 1871665 dated Sep. 9, 2019, 2 pages.

Office Action on JP Application No. 2019-202509 dated Jan. 18, 2021.

Office Action on JP Application No. 2019-202510 dated Jan. 18, 2021.

Second office action issued in Chinese Application No. 201911147244.1 dated Sep. 3, 2021.

\* cited by examiner

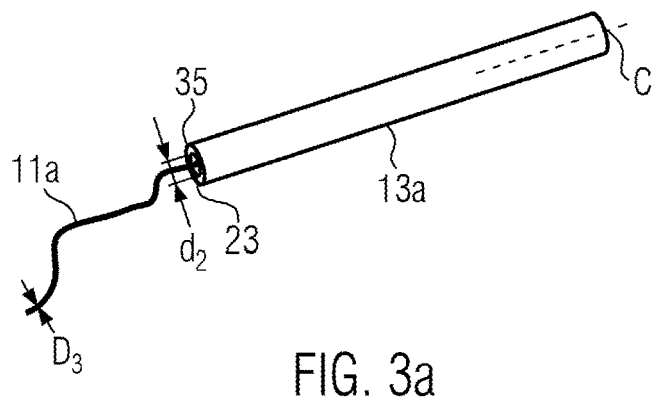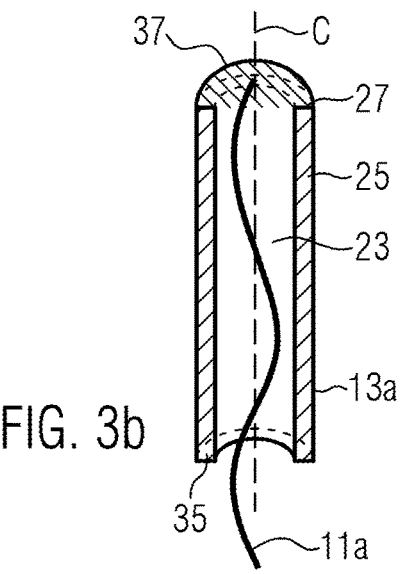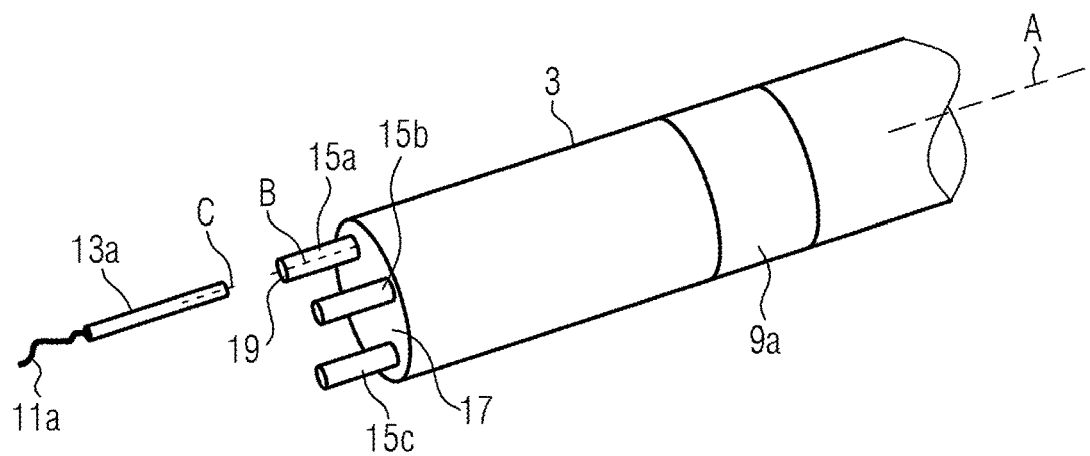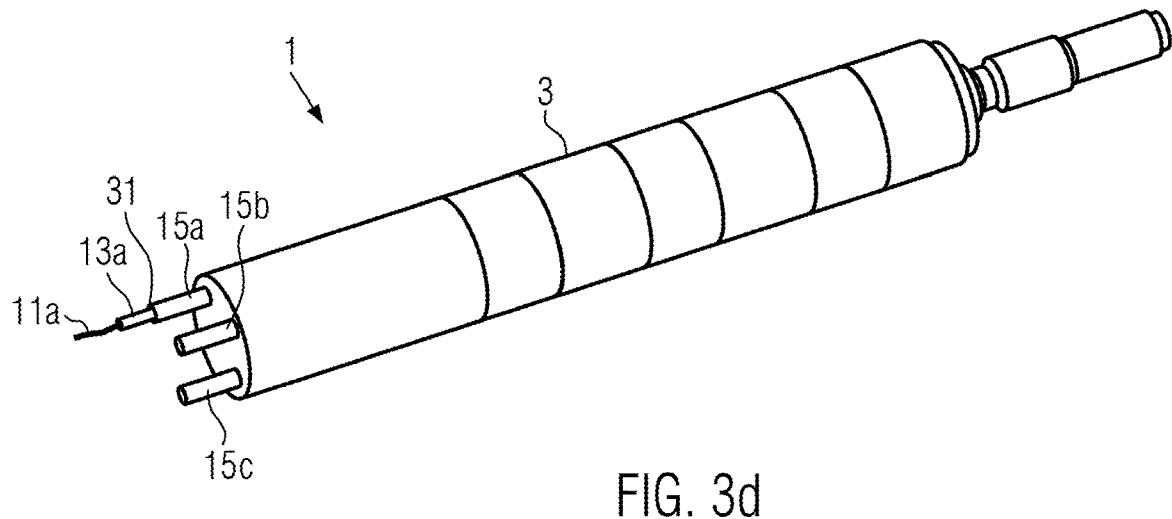

IMPLANTABLE LEAD

CROSS-REFERENCE TO RELATED APPLICATION

This application claims the benefit of and priority to French Application No. 1871664, filed Nov. 21, 2018, which is incorporated herein by reference in its entirety.

BACKGROUND

The present invention relates to an implantable lead, as well as to a method, for electrically connecting at least one conductor of the implantable lead to a connector, in particular to a connector intended to be connected to a cardiac stimulation, defibrillation and/or neuromodulation device.

Such leads for implantable medical devices, such as the implantable lead 100 illustrated in FIG. 1, usually comprise an elongated lead body 101 with four electrodes 102, 103, 104, 105 towards the distal end 106 configured to measure one or several cardiac parameters and/or stimulate cardiac tissue, as well as conductive wires 107a-d and a connector 108 at the proximal end 109 to allow electrical connection with a connection block 110 of a housing 111 of an implantable medical device 112.

The electrical connection between the conductive wires 107a-d of the lead 100 and the connector 108 at the proximal end 113 of the connector 108 is made via one or more hypotubes 114 themselves electrically connected to four electrical contacts (not visible in FIG. 1) of the connector 109. The hypotubes 114 are generally tubes made on an alloy for medical use such as MP35N, platinum or stainless steels, commonly used, for example in the manufacture of medical devices. The electrical connection of the conductive wires 107a-d to the electrical connector 108 is commonly performed by welding, or crimping, of the conductive wires 107a-d to the hypotubes 114 of the connector 108.

However, the welding or crimping of the medical conductors are connection means that may damage the conductive wires of the lead, in particular because of the applied mechanical stress or the energy released by these connection means on the conductive wires. The risk of damaging the wires is notably increased when the conductive wires of the lead have a diameter of less than 150 micrometers, i.e. 0.45 French.

SUMMARY

The object of the present invention is thus to facilitate and secure the electrical connection of the conductive wire of the lead to the connector to improve the reliability of the electrical connection between the electrical wire and the connector of the lead.

The object of the invention is achieved by an implantable lead comprising at least one conductive wire and one electrical connector, the electrical connector configured to be connected to an implantable medical device such as a cardiac stimulation device, a defibrillation device or/and a neuromodulation device; wherein the electrical connection between the conductive wire and the connector is formed by a first hypotube welded to the conductive wire and welded to a second hypotube of the electrical connector. The use of a first hypotube, as an intermediate between the wire conductor and the second hypotube of the electrical connector, can simplify and facilitate the realization of the electrical connection between the conductive wire, which becomes increasingly thin, and the electrical connector.

The implantable lead according to the present invention can be further improved thanks to the following embodiments.

According to another embodiment of the invention, the first hypotube may be partially housed in the second hypotube of the electrical connector such that a portion of the first hypotube protrudes out of the second hypotube. The dimensions of the first hypotube make it possible to accommodate the difference in size between the internal diameter of the second hypotube of the connector and the diameter of the conductive wire.

As a result, the electrical contact can easily be made between the two hypotubes when the first hypotube protrudes out of the second hypotube. In addition, the first hypotube facilitates the realization of the electrical connection of a conductive wire to a connector, even when the diameter of the conductive wire is significantly smaller than the internal diameter of the second hypotube of the connector, in particular about three times smaller.

According to another embodiment of the invention, the first hypotube may be welded to the second hypotube of the electrical connector so as to electrically connect the first hypotube to the second hypotube. The electrical connection between the first and the second hypotube can thus be easily achieved, through a weld. In addition, when a portion of the first hypotube protrudes out of the second hypotube, the realization of the weld between the first hypotube and the second hypotube is facilitated because it can be performed outside the second hypotube.

According to another embodiment of the invention, the welding between the at least one conductive wire and the first hypotube can be made at a first end of the first hypotube through which the at least one conductive wire and/or at a second end of the first hypotube is inserted, the second end being opposite to the first end. As a result, an operator has the choice as to the end of the first hypotube(s) on which to perform the welding because the nature of the electrical contact between the first hypotube and the lead turns out to be the same whatever the end of the first hypotube welded to the conductive wire. In addition, when the welding is performed at both ends of the first hypotube, the risk of malfunction, especially in terms of electrical connection, is reduced by the redundancy of the weld.

According to another embodiment of the invention, the lead may comprise a plurality of conductive wires such that each conductive wire is electrically connected to a respective first hypotube. According to one variant, the lead may comprise several conductive wires, such that at least two conductive wires are electrically connected to the same first hypotube. As a result, the first hypotube is as well adapted to be welded to a conductive wire as to at least two conductive wires, which widens the possibilities of application of the first hypotube according to the invention for an implantable lead.

According to another embodiment of the invention, the weld or welds made to establish the electrical connections may be laser welds. Laser welding makes it possible to achieve a waterproof weld, and also allows precise welding particularly suited to the scale of implantable lead connectors of medical devices. In addition, the laser welding being performed at one or more ends of the first hypotube, and not directly on the lead, the risk of damaging or destroying the conductive wire because of the energy released by the laser beam is reduced.

According to another embodiment of the invention, the at least one conductive wire may be a single strand or multi-stranded conductive wire such that the conductive wire has a diameter less than 150 microns. The first hypotube allows to connect a wire conductor whose diameter is significantly smaller than that of a hypotube of the connector, in particular three to six times smaller for a conductive wire, and whose standard internal diameter of a connector hypotube is generally between 300 and 500 micrometers, or between 0.9 and 1.5 French. Thus, during the electrical connection of conducting wire to a diameter of less than 150 micrometers, the first hypotube makes it possible to accommodate the difference in size between the internal diameter of the hypotube of the connector and the diameter of the conductive wire.

The object of the present invention is also achieved by a method for electrically connecting at least one conductive wire of an implantable lead to an electrical connector, the electrical connector configured to be connected to an implantable medical device such as a cardiac stimulation device, a defibrillation device and/or a neuromodulation device. The method comprises the steps of housing the at least one conductive wire of the lead in a first hypotube, electrically connecting the at least one conductive wire to the first hypotube, at least partially housing the first hypotube in a second corresponding hypotube of the electrical connector, and electrically connecting the first hypotube with the second hypotube.

As a result, the first hypotubes make it possible to make electrical connections with a reduced risk of directly damaging the conductive wires of the lead during welding. Indeed, each wire of the lead is previously housed in a first hypotube being thus protected during the electrical connection. In addition, this step of electrical connection between the conductive wire and the first hypotube is easier to achieve than an electrical connection when the conductive wire is directly introduced into the second hypotube of the connector. Thus, the first hypotubes also facilitate assembly and electrical connection of the conductive wire to the connector.

The present invention, relating to a method for electrically connecting at least one conductive wire of an implantable lead to an electrical connector, can be further improved by the following embodiments.

According to another embodiment of the invention, one or more of the electrically connecting steps may comprise performing a laser weld. Thus, as the lead is protected by the first hypotube, the laser beam of the weld does not directly reach the wire itself, which could—depending on the diameter of the wire—damage it, or destroy it. In addition, the laser welding allows the formation of a smooth and rounded surface at one or the two ends of the first hypotube, which further improves the quality of the electrical connection.

According to another embodiment of the invention, the welding can be performed at a first end of the first hypotube by which is inserted the at least one conductive wire and/or at a second end of the first hypotube, the second end opposite the first end. As a result, an operator has the choice as to the end(s) of the first hypotube on which to realize the welding because the nature of the electrical contact between the first hypotube and the wire turns out to be the same whatever the end of the first hypotube welded to the wire. In addition, when the welding is performed at both ends of the first hypotube, the risk of malfunction, especially in terms of electrical connection, is reduced by the redundancy of the weld.

According to another embodiment of the invention, partially housing the first hypotube in the second hypotube may comprise the insertion of the first hypotube into the second hypotube so that a portion of the first hypotube protrudes out of the second hypotube. Thus, the realization of the welding between the first hypotube and the second hypotube is facilitated because it can be performed outside the second hypotube, providing more space and visibility for an operator to perform the weld.

Embodiments may be combined to form more advantageous alternative embodiments of the present invention.

BRIEF DESCRIPTION OF THE DRAWINGS

The invention and its advantages will be explained in more detail in the following by means of preferred embodiments and relying in particular on the following example figures, in which:

FIG. 2b shows a sectional view of the implantable lead e shown in FIG. 2a.

FIG. 3a represents a step of the method for electrically connecting a conductive wire of an implantable lead to an electrical connector according to an embodiment of the present invention.

FIG. 3b represents a step of the method for electrically connecting a conductive wire of an implantable lead to an electrical connector according to an embodiment of the present invention.

FIG. 3c represents a step of the method for electrically connecting a conductive wire of an implantable lead to an electrical connector according to an embodiment of the present invention.

FIG. 3d represents a step of the method for electrically connecting a conductive wire of an implantable lead to an electrical connector according to an embodiment of the present invention.

DETAILED DESCRIPTION

The invention will now be described in more detail using advantageous embodiments in an exemplary method and with reference to the drawings. The described embodiments are merely possible configurations and it should be borne in mind that the individual features as described above may be provided independently of each other or may be omitted altogether when the implementation of the present invention.

Figure 1:
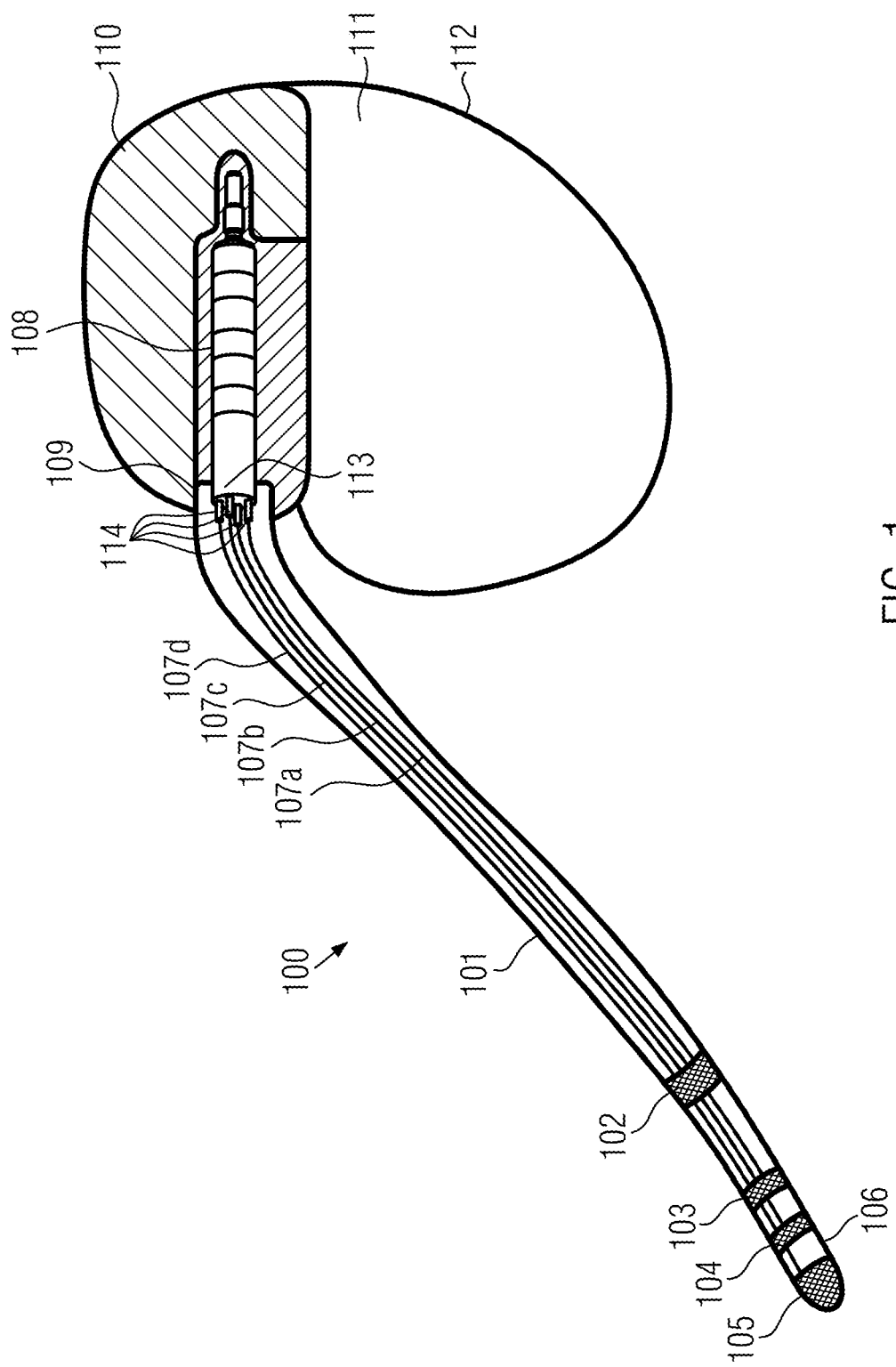
FIG. 1 schematically shows an implantable lead according to the prior art.
Figure 2A:
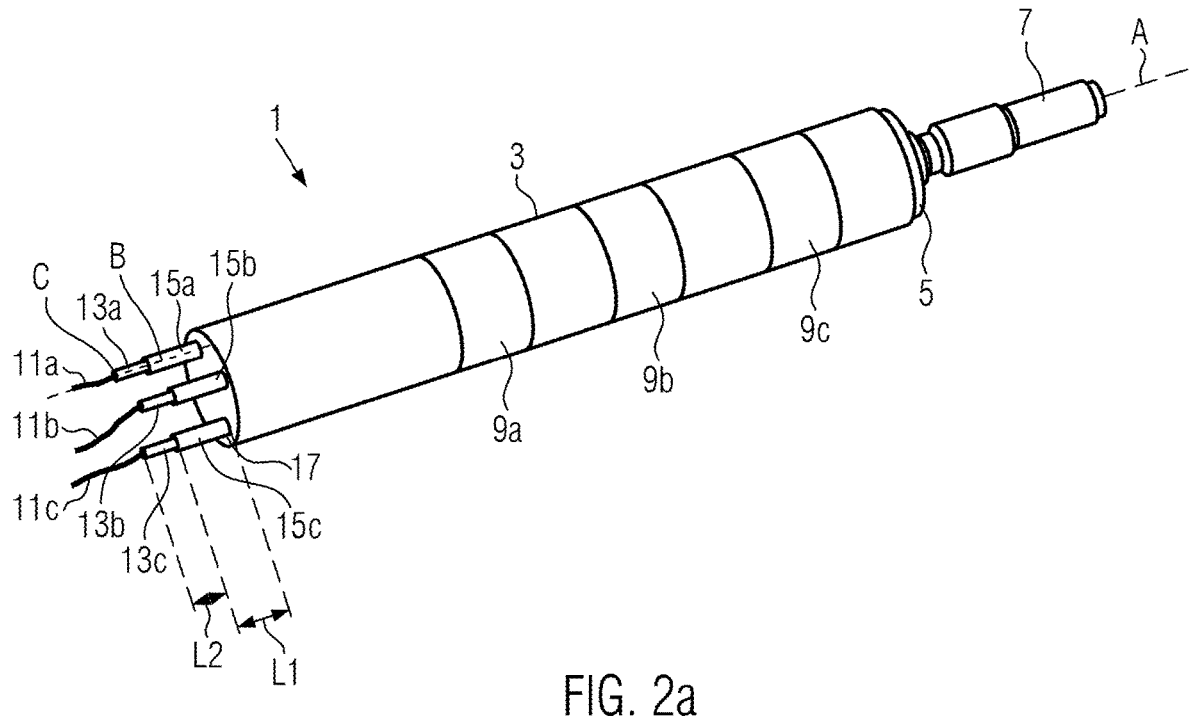
FIG. 2a represents a partial view of the implantable lead according to the present invention.

FIG. 2a schematically illustrates a partial view of an implantable lead 1 at its proximal end. FIG. 2a shows a connector 3 of the implantable lead 1. The connector 3 has a cylindrical shape of axis A and comprises at its distal end 5 a distal pin 7 configured to be connected to a terminal of an implantable medical device (not shown) such as a cardiac pacing, defibrillation, and/or neuromodulation device.

The connector 3 shown in FIG. 2a is of multipolar type because it is provided with three contacts 9a, 9b, 9c. In a variant, the connector 3 may comprise more or less than three contacts. In another variant, the connector 3 may comprise only one contact.

The connector 3 can be made from biocompatible conductive materials such as 316L stainless steel or a metal alloy, MP35N, for example. The material of connector 3 can be selected to be biocompatible, conductive and to suitably transmit electrical signals from an electrical stimulation device (not shown).

The implantable lead 1 also comprises conductive wires 11a, 11b, 11c which allows electrical connection of the contacts 9a, 9b, 9c of the connector 3 to one or several electrodes (not shown) of the lead 1. In the illustrated embodiment illustrated in FIG. 2a, the conductive wires 11a, 11b, 11c are each multi-stranded conductive wires such that the diameter of each multi-stranded conductive wire 11a, 11a, 11c is less than 150 micrometers. The individual conductive wires each constituting multi-stranded conductive wires 11a, 11b, 11c are not electrically isolated from each other. However, the multi-stranded conductive wires 11a, 11b, 11c are electrically isolated from each other.

In a variant, the conductive wires 11a, 11b, 11c are single conductive wires such that the diameter of each conductive wire 11a, 11b, 11c, that is to say of each single-wire conductive wire, is less than 150 micrometers. In addition, single conductive wires 11a, 11b, 11c are electrically isolated from each other.

According to the present invention, the conductive wires 11a, 11b, 11c are each housed and welded to a first hypotube 13a, 13b, 13c; and each first hypotube 13a, 13b, 13c is itself housed and welded to a second hypotube 15a, 15b, 15c of the connector 3 at the proximal end 17 of the connector 3.

The axis A of the connector 3 is parallel to the respective axes B, C of the second hypotubes 15a, 15b, 15c and of the first hypotube 13a, 13b, 13c. The axis C of each first hypotube 13a, 13b, 13c coincides with the axis B of the second hypotube 15a, 15b, 15c in which it is inserted.

The second hypotubes 15a, 15b, 15c are housed in the connector 3 and electrically connected with the contacts 9a, 9b, 9c. A length portion L1 of each second hypotube 15a, 15b, 15c protrudes out of the connector 3.

The first hypotubes 13a, 13b, 13c are housed in a second corresponding hypotube 15a, 15b, 15c so that a portion of length L2 of each first hypotube 13a, 13b, 13c protrudes out of the second hypotube 15a, 15b, 15c.

Alternatively, several conductive wires can be housed in the same first hypotube. The number of first hypotubes, of second hypotubes and of conductive wires, each of which is three in the implantable lead 1 shown in FIG. 2a, is thus illustrative and does not constitute a numerical limitation of the present invention.

Figure 2B:
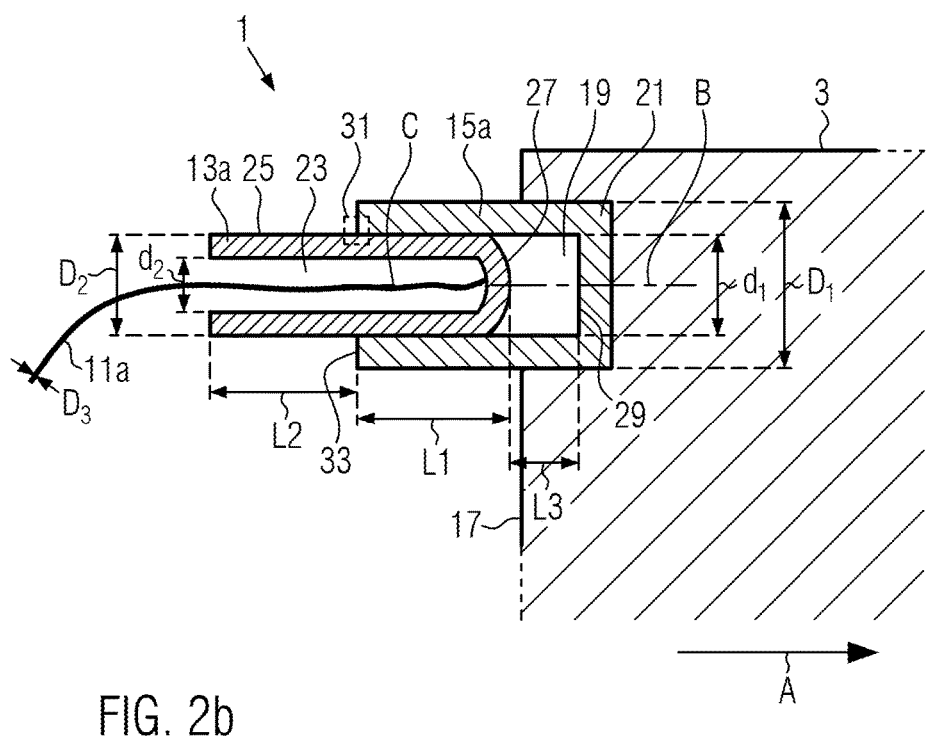

FIG. 2a will be further described in the following in combination with FIG. 2b which illustrates a partial sectional view of the lead 1. Even though FIG. 2b illustrates only one of the first and second hypotubes 13a, 15a of FIG. 2a, the description of the hypotubes 13a, 15a also applies to the other hypotubes 13b, 13c, 15b, 15c of the implantable lead 1. The elements with the same numeral references already used for the description of FIG. 2a will not be described in detail and reference is made to their descriptions above.

FIG. 2b shows the second hypotube 15a which is partially housed in the connector 3. The second hypotube 15a is electrically connected (not shown) to one of the contacts 9a, 9b, 9c of the connector 3. The second hypotube 15a comprises a hollow portion 19 of internal diameter d1 and a wall 21 made of stainless steel. The second hypotube 15a has an outer diameter D1.

The first hypotube 13a also comprises a hollow portion 23 the internal diameter of which is d2 and a wall 25 made of stainless steel. The second hypotube 15a has an outer diameter D2.

The outer diameter D2 of the first hypotube 13a is less than or equal to the internal diameter d1 of the second hypotube 15a so that it is possible to insert the first hypotube 13a in the hollow portion 19 of the second hypotube 15a. As illustrated in FIG. 2b, the outer diameter D2 of the first hypotube 13a is dimensioned so that the wall 25 of the first hypotube 13a is in contact with the wall 21 of the second hypotube 15a in order to improve the electrical contact and the maintaining the first hypotube 13a in the second hypotube 15a.

The diameter D3 of the conductive wire 11a is smaller than the internal diameter d2 of the first hypotube 13a. In particular, the conductive wire 11a according to the present invention has a diameter D3 of less than 150 micrometers. The internal diameter d2 of the first hypotube 13a comprised between 150 micrometers and 350 micrometers. Thus, the dimensions d2, D2 of the first hypotube 13a make it possible to accommodate the difference in size between the internal diameter d of the second hypotube 15a of the connector 3 and the diameter D3 of the conductive wire 11a. Therefore, the first hypotube 13a, in addition to allowing an electrical connection, is also a means of adaptation to accommodate the difference in size between the conductive wire 11a and the second hypotube 15a of connector 3.

In the embodiment illustrated in FIG. 2b, the conductive wire 11a is inserted into the hollow portion 23 of the first hypotube 13a and is welded at one end 27 of the first hypotube 13a. The welding of the lead 11a to the first hypotube 13a will be further described with reference to FIG. 3b.

In the embodiment illustrated in FIG. 2b, the first hypotube 13a is partially housed in the second hypotube 15a so that there is a distance L3 between the end 27 of the first hypotube 13a and a closed end 29 of the second hypotube 15a.

According to another embodiment, the first hypotube 13a can be inserted as far as a stop in the second hypotube 15a, so that there is contact between the end 27 of the first hypotube 13a and the closed end 29 of the second hypotube 15a. Alternatively, not shown in FIG. 2b, the end 29 of the second hypotube 15a may be a partially closed end or an open end.

The first hypotube 13a is welded to the second hypotube 15a outside the connector 3 at a junction zone 31 located between the wall 25 of the first hypotube 13a and an open end 33 of the second hypotube 15a. Thus, achieving the weld between the first hypotube 13a and the second hypotube 15a is facilitated because it can be performed outside the second hypotube 15a and connector 3, providing more space and visibility to an operator to perform the weld. In addition, the weld zone 31 between the first hypotube 13a and the corresponding second hypotube 15a is distinct from the weld zones of the other first hypotubes 13b, 13c and of their respective second hypotubes 15b, 15c (see FIG. 2a, not shown in FIG. 2b). Thus, an operator may, for example, perform the electrical connection at the first hypotube 13a without having to rework the electrical connections of the other first hypotubes 13b, 13c.

According to an embodiment of the present invention, the welding between the conductive wire 11a and the first hypotube 13a, as well as the welding at the junction zone 31 between the first hypotube 13a and the second hypotube 15a are performed by laser welding. Laser welding notably makes it possible to achieve a sealed weld, and also allows precise welding particularly suitable for the scale of implantable lead connectors of medical devices.

FIGS. 3a to 3d schematically illustrate steps of the method for electrically connecting the conductive wire 11a of the implantable lead 1 to the connector 3 according to another embodiment.

The elements with the same numerical references already used for the description of FIGS. 2a and 2b will not be described again in detail, and reference is made to their descriptions above.

FIG. 3a illustrates the first step in which the lead 11a is inserted through an open end 35 of the first hypotube 13a into the hollow portion 23 of the first hypotube 13a. In one variant, a plurality of conductive wires may be introduced into the first hypotube 13a.

According to the embodiment illustrated in FIG. 3a, the conductive wire 11a has a diameter D3 of less than 150 micrometers and the hollow portion 23 of the first hypotube 13a has an internal diameter d2 of between 150 and 350 micrometers.

FIG. 3b illustrates a longitudinal sectional view along the axis C of the first hypotube 13a at the step wherein the conductive wire 11a is welded to the first hypotube 13a to electrically connect them.

According to the embodiment illustrated in FIG. 3b, the conductive wire 11a has been introduced through the open end 35 of the first hypotube 13a to the end 27 opposite the end 35; and welded at the end 27 of the first hypotube 13a.

According to other embodiments, the conductive wire 11a may be welded at the end 35 of the first hypotube 13a, by which the conductor 11a is introduced, or at both ends 27, 35 of the first hypotube 13a, as long as a connection between the conductive wire 11a and the hypotube 13a is permitted.

The welding between the conductive wire 11a and the first hypotube 13a is performed by a laser weld. Thus, a smooth and rounded surface 37 is formed at the end 27 of the first hypotube 13a and the electrical contact between the conductive wire 11a and the first hypotube 13a is obtained.

The laser beam is not directed and applied directly to the lead 11a, but on one end 27, 35 of the first hypotube 13a in which the lead 11a is housed, the risk of damaging or destroying the conductive wire 11a, especially when its diameter is less than 150 micrometers, because of the energy released by the laser beam, is reduced.

FIG. 3c illustrates the insertion step of the first hypotube 13a to which the conductive wire 11a is welded.

The end 27 of the first hypotube 13a is inserted into the hollow portion 19 of the second hypotube 19 so that a portion of length L2 of the first hypotube 13a remains outside the second hypotube 15a, as illustrated in FIGS. 2a and 2b.

The next step of the method for electrically connecting the conductive wire 11a of the implantable lead 1 to the connector 3 is illustrated in FIG. 3d.

This step consists of welding the first hypotube 13a to the second hypotube 15a at the junction 31 located outside the connector 3. This step allows to electrically connect the second hypotube 15a of the connector 3 to the first hypotube 13a, itself electrically connected to the conductive wire 11a during the step illustrated in FIG. 3b. Thus, the first hypotube 13a serves as an intermediate for the electrical connection between the conductive wire 11a and the second hypotube 15a of the connector 3.

The use of the first hypotube 13a, making it possible to make the intermediate between the conductive wire 11a and the connector 3, then makes possible an electrical connection between a connector comprising a hypotube with standard dimensions of between 350 and 500 micrometers and a conductive wire of diameter less than 150 micrometers.

The description of the steps for electrically connecting the conductive wire 11a to the connector 3 of the lead 1 with reference to FIGS. 3a to 3d applies integrally to the connection of the conductive wires 11b and 11c to the connector 3 of the lead.

Those skilled in the art will appreciate that the present invention can be applied essentially to any type of implantable lead whose electrical connector is provided with at least one hypotube.

What is claimed is:

1. An implantable lead comprising:
 a plurality of conductive wires, wherein each of the plurality of conductive wires are multi-stranded conductive wires, and wherein each of the plurality of conductive wires has a diameter of less than 150 microns or 0.45 French; and
 an electrical connector comprising a plurality of first hypotubes, a plurality of second hypotubes and a plurality of electrical contacts on an outer surface of the electrical connector, the electrical connector configured to be connected to an implantable medical device via the plurality of electrical contacts, wherein:
 a plurality of electrical connections are formed between the plurality of conductive wires and the electrical connector, wherein each electrical connection includes:
  a welded electrical connection between a first hypotube and a conductive wire;
  a welded electrical connection between the first hypotube and a second hypotube; and
  the second hypotube is electrically connected to an electrical contact of the plurality of electrical contacts, such that the conductive wire is inserted into and welded to the first hypotube, the first hypotube is inserted into and welded to the second hypotube, and the second hypotube is inserted into and welded to the electrical contact.

2. The implantable lead according to claim 1, wherein the first hypotube is partially housed in the second hypotube such that a portion of the first hypotube protrudes out of the second hypotube.

3. The implantable lead of claim 1, wherein the welded electrical connection between the conductive wire and the first hypotube is made at a first end of the first hypotube or at a second end of the first hypotube, the second end being opposite the first end.

4. The implantable lead of claim 1, wherein at least one of the welded electrical connection between the first hypotube and the conductive wire and the welded electrical connection between the first hypotube and the second hypotube is formed by laser welding.

5. A method for electrically connecting a plurality of conductive wires of an implantable lead to an electrical connector, the electrical connector configured to be connected to an implantable medical device via a plurality of electrical contacts on an outer surface of the electrical connector, the method comprising the steps of:
 forming a plurality of electrical connections between the plurality of conductive wires and the electrical connector, wherein each of the plurality of conductive wires are multi-stranded conductive wires, and wherein each of the plurality of conductive wires has a diameter of less than 150 microns or 0.45 French, and each electrical connection formed by:
  housing a conductive wire in a first hypotube;
  electrically connecting the conductive wire to the first hypotube via welding;
  at least partially housing the first hypotube in a corresponding second hypotube of the electrical connector, the second hypotube electrically connected to an electrical contact of the plurality of electrical contacts; and electrically connecting the first hypotube with the second hypotube via welding, such that the conductive wire is inserted into and welded to the first hypotube, the first hypotube is inserted into and welded to the second hypotube, and the second hypotube is inserted into and welded to the electrical contact.

6. The method for of claim 5, wherein one or more of the electrically connecting steps comprises performing a laser weld.

7. The method of claim 6, wherein the conductive wire is welded to the first hypotube at a first end of the first hypotube through which the conductive wire is inserted and/or at a second end of the first hypotube, the second end opposed to the first end.

8. The method of claim 6, wherein partially housing the first hypotube in the second hypotube comprises inserting the first hypotube into the second hypotube such that a portion of the first hypotube protrudes out of the second hypotube.

9. An implantable medical device for cardiac pacing, defibrillation, or neuromodulation comprising:
   an implantable lead comprising an electrical connector and a plurality of conductive wires electrically connected to the electrical connector, wherein each of the plurality of conductive wires are multi-stranded conductive wires, and wherein each of the plurality of conductive wires has a diameter of less than 150 microns or 0.45 French, and the electrical connector comprising a plurality of electrical contacts on its outer surface along with a plurality of first hypotubes and a plurality of second hypotubes, wherein each of the plurality of first hypotubes has a diameter between 150 and 350 microns, and wherein:
   a plurality of electrical connections are formed between the plurality of conductive wires and the electrical connector, wherein in each electrical connection:
      a welded electrical connection between a first hypotube and a conductive wire;
      a welded electrical connection between the first hypotube and a second hypotube; and
      the second hypotube is electrically connected to an electrical contact of the plurality of electrical contacts such that the conductive wire is inserted into and welded to the first hypotube, the first hypotube is inserted into and welded to the second hypotube, and the second hypotube is inserted into and welded to the electrical contact.

10. The implantable medical device of claim 9, wherein the first hypotube is partially housed in the second hypotube such that a portion of the first hypotube protrudes out of the second hypotube.

11. The implantable medical device of claim 9, wherein the welded electrical connection between the conductive wire and the first hypotube is made at a first end of the first hypotube or at a second end of the first hypotube, the second end being opposite the first end.

* * * * *